(12) United States Patent
Popovich et al.

(10) Patent No.: US 8,460,524 B2
(45) Date of Patent: Jun. 11, 2013

(54) SYSTEM AND METHODS OF CHEMISTRY PATTERNING FOR A MULTIPLE WELL BIOSENSOR

(75) Inventors: Natasha Popovich, Pompano Beach, FL (US); Gary T. Neel, Weston, FL (US); William Milo, Fort Lauderdale, FL (US); Zachary Thomas, Germantown, TN (US); Stephen Davies, Tamarac, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 1068 days.

(21) Appl. No.: 12/102,218

(22) Filed: Apr. 14, 2008

(65) Prior Publication Data
US 2009/0038939 A1 Feb. 12, 2009

Related U.S. Application Data

(60) Provisional application No. 60/912,500, filed on Apr. 18, 2007.

(51) Int. Cl.
*G01N 27/327* (2006.01)
(52) U.S. Cl.
USPC .................. 204/403.14; 205/777.5; 205/792; 438/1; 438/48
(58) Field of Classification Search
USPC ................. 204/400–403.15; 205/777.5, 778, 205/792; 600/345–348; 438/48, 1
See application file for complete search history.

(56) References Cited

U.S. PATENT DOCUMENTS

| 5,466,575 | A | 11/1995 | Cozzette et al. |
| 2003/0203498 | A1 | 10/2003 | Neel et al. |
| 2003/0212344 | A1* | 11/2003 | Yuzhakov et al. ............ 600/583 |
| 2004/0040866 | A1* | 3/2004 | Miyashita et al. ......... 205/777.5 |
| 2004/0045821 | A1* | 3/2004 | Cui et al. .................. 204/403.02 |

(Continued)

FOREIGN PATENT DOCUMENTS

| EP | 1 380 837 A1 | 1/2004 |
| EP | 1 650 560 A1 | 4/2006 |

(Continued)

OTHER PUBLICATIONS

Revzin et al. (Sensors and Actuators B, 81, 2002, 359-368).*

(Continued)

*Primary Examiner* — J. Christopher Ball
*Assistant Examiner* — Jennifer Dieterle
(74) *Attorney, Agent, or Firm* — Finnegan, Henderson, Farabow, Garrett & Dunner LLP

(57) ABSTRACT

Methods and systems for measuring the concentration of an analyte in a blood sample and, more particularly, to methods of chemistry patterning reagent layers for multiple well biosensors. A first capillary is first configured to receive a dispensed reagent layer such that the reagent layer is distributed in a substantially uniform manner within the first capillary. The first capillary may also configured to isolate the first capillary from other capillaries present in the biosensor. After the reagent layer has been dispensed and dried, the first capillary may then be reconfigured to allow the first capillary to receive a blood sample.

12 Claims, 11 Drawing Sheets

U.S. PATENT DOCUMENTS

| | | | |
|---|---|---|---|
| 2004/0067166 A1* | 4/2004 | Karinka et al. | 422/82.03 |
| 2004/0094433 A1* | 5/2004 | Neel et al. | 205/777.5 |
| 2004/0211666 A1* | 10/2004 | Pamidi et al. | 204/403.01 |
| 2005/0013731 A1* | 1/2005 | Burke et al. | 422/56 |
| 2005/0023137 A1* | 2/2005 | Bhullar et al. | 204/403.1 |
| 2005/0023152 A1* | 2/2005 | Surridge et al. | 205/775 |
| 2005/0224345 A1* | 10/2005 | Taniike et al. | 204/403.01 |
| 2005/0247573 A1* | 11/2005 | Nakamura et al. | 205/777.5 |
| 2007/0131565 A1* | 6/2007 | Fujiwara et al. | 205/777.5 |
| 2007/0173740 A1* | 7/2007 | Chan et al. | 600/583 |
| 2008/0073208 A1* | 3/2008 | Wang et al. | 204/406 |

FOREIGN PATENT DOCUMENTS

| | | | |
|---|---|---|---|
| WO | WO 02/18933 A2 | | 3/2002 |
| WO | WO 2004/113910 A1 | | 12/2004 |
| WO | WO 2005-054840 | * | 6/2005 |
| WO | WO 2008/030757 A1 | | 3/2008 |

OTHER PUBLICATIONS

International Search Report of PCT/US2008/060330, dated Jul. 31, 2008.

* cited by examiner

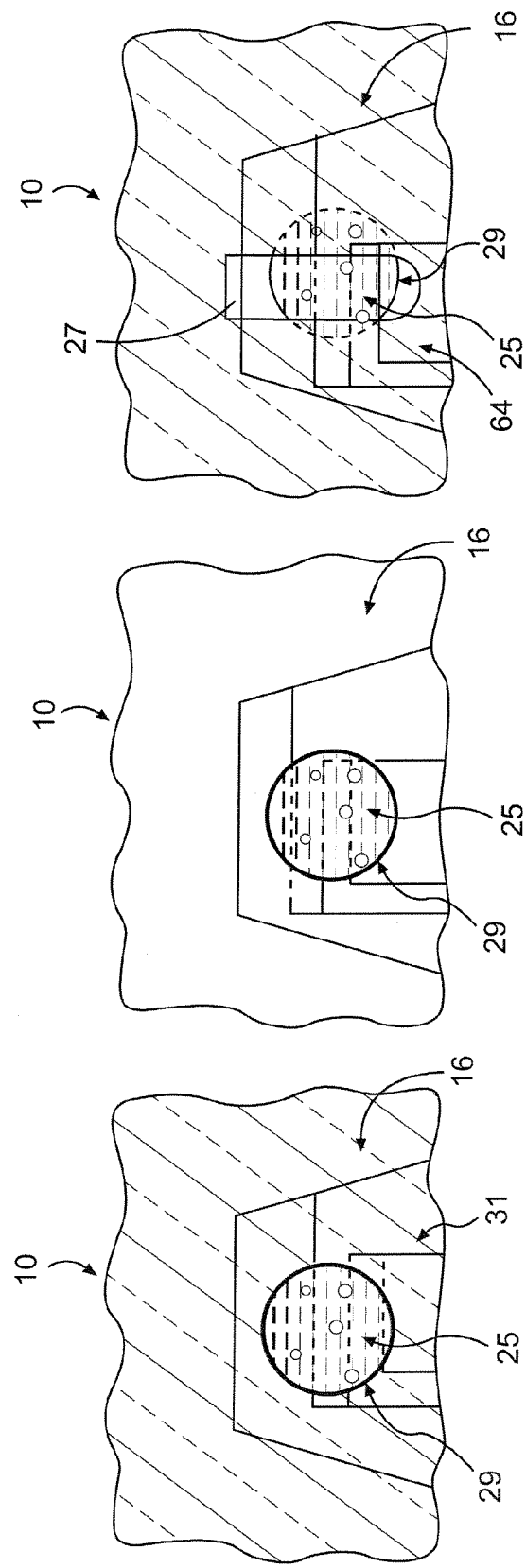

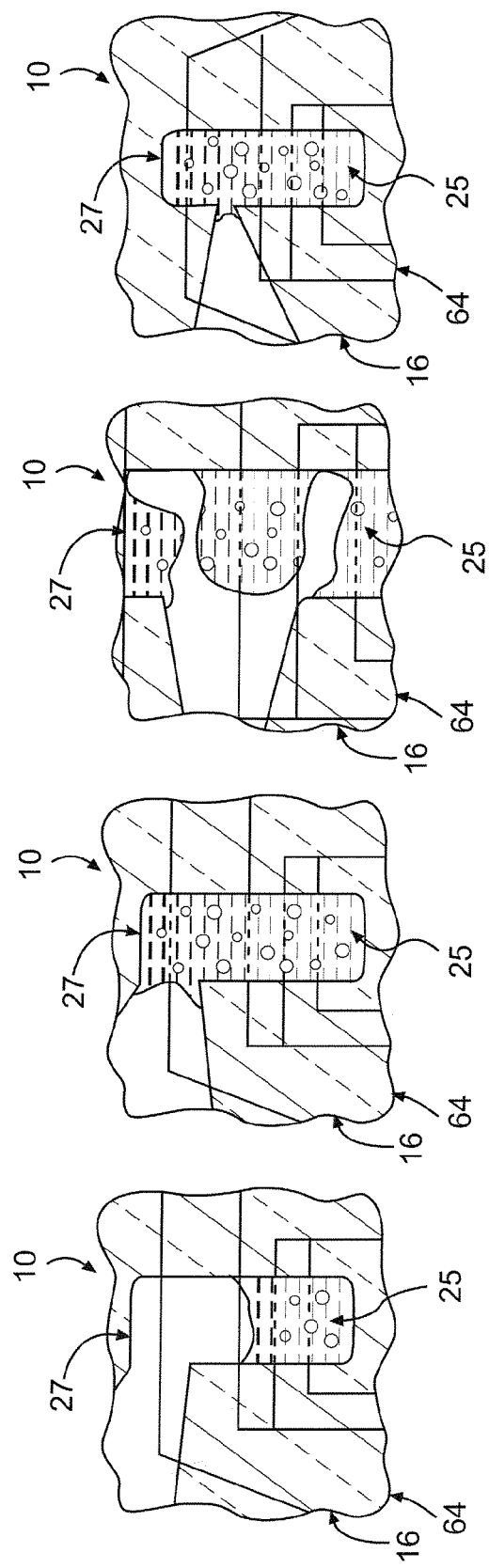

SYSTEM AND METHODS OF CHEMISTRY PATTERNING FOR A MULTIPLE WELL BIOSENSOR

This application claims priority to U.S. Provisional Patent Application No. 60/912,500 filed on Apr. 18, 2007, the content of which is incorporated herein by reference.

FIELD OF THE INVENTION

The present invention relates to the field of diagnostic testing systems for measuring the concentration of an analyte in a blood sample and, more particularly, to methods of chemistry patterning reagent layers for multiple well biosensors.

BACKGROUND OF THE INVENTION

The present disclosure relates to a biosensor system for measuring an analyte in a bodily fluid, such as blood, wherein the system comprises processes and systems for the deposition of reagents into multiple well biosensors. For example, the present disclosure provides methods of applying a chemistry solution within a well (e.g. sample cavity, sample chamber, or capillary), of a biosensor to enable the measurement of a specific analyte of a blood sample such as, for example, blood ketones, hemoglobin A1c, cholesterol, hematocrit, and triglicerides. Further, the biosensor system may contain additional wells to enable the measurement of additional blood analytes. While described herein in relation to blood constituent testing, the invention can be used to measure analytes in other fluid samples as well.

Electrochemical sensors have long been used to detect and/or measure the presence of substances in a fluid sample. In the most basic sense, electrochemical sensors comprise a reagent mixture containing at least an electron transfer agent (also referred to as an "electron mediator") and an analyte specific bio-catalytic protein (e.g. a particular enzyme), and one or more electrodes. Such sensors rely on electron transfer between the electron mediator and the electrode surfaces and function by measuring electrochemical redox reactions. When used in an electrochemical biosensor system or device, the electron transfer reactions are transformed into an electrical signal that correlates to the concentration of the analyte being measured in the fluid sample.

The use of such electrochemical sensors to detect analytes in bodily fluids, such as blood or blood-derived products, tears, urine, or saliva, has become important, and in some cases, vital, to maintain the health of certain individuals. In the health care field, people such as diabetics, for example, have a need to monitor a particular constituent within their bodily fluids. A number of systems are available that allow people to test a body fluid, such as, blood, urine, or saliva, to conveniently monitor the level of a particular fluid constituent, such as, for example, cholesterol, proteins, and glucose. Patients suffering from diabetes, a disorder of the pancreas where insufficient insulin production prevents the proper digestion of sugar, have a need to carefully monitor their blood glucose levels on a daily basis. Routine testing and controlling blood glucose for people with diabetes can reduce their risk of serious damage to the eyes, nerves, and kidneys.

A number of systems permit people to conveniently monitor their blood glucose levels, and such systems typically include a test strip where the user applies a blood sample and a meter that "reads" the test strip to determine the glucose level in the blood sample. An exemplary electrochemical biosensor is described in U.S. Pat. No. 6,743,635 ('635 patent) which is incorporated by reference herein in its entirety. The '635 patent describes an electrochemical biosensor used to measure glucose level in a blood sample. The electrochemical biosensor system is comprised of a test strip and a meter. The test strip includes a sample chamber, a working electrode, a counter electrode, and fill-detect electrodes. A reagent layer is disposed in the sample chamber. The reagent layer contains an enzyme specific for glucose, such as, glucose oxidase, and a mediator, such as, potassium ferricyanide or ruthenium hexaamine. When a user applies a blood sample to the sample chamber on the test strip, the reagents react with the glucose in the blood sample and the meter applies a voltage to the electrodes to cause redox reactions. The meter measures the resulting current that flows between the working and counter electrodes and calculates the glucose level based on the current measurements.

Biosensors configured to measure a blood constituent may be affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the particular blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrits, while a positive bias (i.e., higher calculated analyte concentration) is observed at low hematocrits. At high hematocrits, for example, the red blood cells may impede the reaction of enzymes and electrochemical mediators, reduce the rate of chemistry dissolution since there less plasma volume to solvate the chemical reactants, and slow diffusion of the mediator. These factors can result in a lower than expected glucose reading as less current is produced during the electrochemical process. Conversely, at low hematocrits, less red blood cells may affect the electrochemical reaction than expected, and a higher measured current can result. In addition, the blood sample resistance is also hematocrit dependent, which can affect voltage and/or current measurements.

Several strategies have been used to reduce or avoid hematocrit based variations on blood glucose readings as described in U.S. patent application Ser. No. 11/401,458 which is incorporated by reference herein in its entirety. For example, test strips have been designed to incorporate meshes to remove red blood cells from the samples, or have included various compounds or formulations designed to increase the viscosity of red blood cell and attenuate the effect of low hematocrit on concentration determinations. Further, biosensors have been configured to measure hematocrit by measuring optical variations after irradiating the blood sample with light, or measuring hematocrit based on a function of sample chamber fill time. These methods have the disadvantages of increasing the cost and complexity of test strips and may undesirably increase the time required to determine an accurate glucose measurement.

In addition, alternating current (AC) impedance methods have also been developed to measure electrochemical signals at frequencies independent of a hematocrit effect. Such methods suffer from the increased cost and complexity of advanced meters required for signal filtering and analysis.

An additional prior hematocrit correction scheme is described in U.S. Pat. No. 6,475,372. In that method, a two potential pulse sequence is employed to estimate an initial glucose concentration and determine a multiplicative hematocrit correction factor. A hematocrit correction factor is a particular numerical value or equation that is used to correct an initial concentration measurement, and may include determining the product of the initial measurement and the determined hematocrit correction factor. Data processing using this technique, however, is complicated because both a hematocrit correction factor and an estimated glucose concentration must be determined to establish the corrected glucose value. In addition, the time duration of the first step greatly increases the overall test time of the biosensor, which is undesirable from the user's perspective.

A further hematocrit correction method is described in U.S. Patent Application No. 60/842,032 filed Sep. 5, 2006, which is incorporated by reference herein in its entirety. In particular, the concept of a low blood volume sensor with multiple sample cavities filled with a single blood drop is disclosed. This arrangement allows for the measurement of multiple analytes within a blood sample, such as hematocrit, in addition to measuring the glucose level. Thus, a corrected glucose level can be determined by taking into account the levels of the other analytes measured in the blood sample.

The measurement of multiple analytes, however, may require the application of different chemistry solutions in various sample cavities. For example, when one of the sample cavities is used for hematocrit measurement by measuring the resistance of the blood sample, it is desirable to measure this resistance in whole blood without any chemical additives in it in order to minimize the background effect from the electrolytes from the reagent chemistry. In contrast, other sample cavities may contain biosensor chemistry solutions containing enzymes specific for the analyte of interest, such as mediators, binders, stabilizers and surfactants. While the actual placement of biosensor chemistry solutions, or biosensor reagents, can be accomplished by means of precision dispensing and machine vision, drop spreading after dispensing is controlled largely by the dimensions and surface properties of the sensor itself and the properties of the biosensor reagent solution.

Typically, a biosensor reagent is formulated with a large amount of the surfactant, to ensure uniform spreading and fast dissolution of the dried chemistry layer upon contact with the blood sample. The presence of surfactants in the biosensor reagent, however, makes it difficult to reproducibly dispense the reagent within a certain area, since the surfactant promotes spreading of the biosensor reagent into an adjacent sample cavity. On the other hand, reducing the amount of surfactant below the optimal concentration results in a non-uniform coating and a negative impact on measurement precision. Further, traditional methods for biosensor reagent application, such as screen printing, rotogravure or flexo printing are not easily applied to the multi-well sensor because of registration issues associated with applying two or more chemistry patterns within a very small area of the sensor.

Accordingly, novel systems and methods for reproducibly and selectively applying a biosensor reagent to a single sample cavity, within a multiple sample cavity biosensor, are needed.

SUMMARY OF THE INVENTION

One illustrative embodiment is directed to a biosensor having a base layer including a first capillary disposed on the base layer configured to electrochemically determine a concentration of a first analyte in a blood sample, and wherein the first capillary includes a first set of at least one electrode. The biosensor also includes a second capillary disposed on the base layer configured to determine a value correlating to a second analyte of the blood sample, and wherein the second capillary includes a second set of at least one electrode. The biosensor also includes a reagent layer at least partially within the first capillary.

Another exemplary embodiment of the invention is directed to a method for manufacturing a biosensor comprising at least partially forming a plurality of electrodes on a generally planar base layer. The method also includes forming a first capillary disposed on the base layer, and wherein the first capillary includes a first set of at least one electrode selected from the plurality of electrodes. Further, the method includes forming a second capillary on the base layer, and wherein the second capillary includes a second set of at least one electrode selected from the plurality of at least partially formed electrodes. Additionally, the method includes the formation of a reagent layer at least partially within the first capillary.

In a further illustrative embodiment of the invention is directed to a reel for manufacturing biosensors comprising a generally planar base layer including a plurality of at least partially formed electrodes. Additionally, the reel includes a first capillary disposed on the base layer, and wherein the first capillary includes a first set of at least one electrode selected from the plurality of electrodes. The reel also includes forming a second capillary on the base layer, and wherein the second capillary includes a second set of at least one electrode selected from the plurality of at least partially formed electrodes. Further, the reel includes a reagent layer at least partially within the first capillary.

Another illustrative embodiment of the invention is directed to a method of manufacturing a plurality of test strips for a biosensor comprising forming a reel containing a base layer. Moreover, the method includes forming a plurality of electrodes on the base layer, and partially forming a test strip, wherein the test strip includes a first capillary on the base layer including at least one of the plurality of electrodes and the test strip further includes a second capillary on the base layer including at least one of the plurality of electrodes. Also, the method includes the formation of a reagent layer at least partially within the first capillary.

A still further exemplary embodiment of the invention is directed to a test card for quality control analysis of biosensors comprising a base layer, wherein the base layer includes a plurality of electrodes. Further, a plurality of partially formed test strips, wherein each test strip includes a first capillary on the base layer including at least one of the plurality of electrodes and each test strip further includes a second capillary on the base layer including at least one of the plurality of electrodes. Moreover, each test strip includes a reagent layer at least partially within the first capillary.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 3A shows an enlarged top view of the tip of a test strip with a sacrificial-spacer layer and a reagent layer.

FIG. 3B shows an enlarged top view of the tip of a test strip with after the removal of the sacrificial-spacer layer and the remaining reagent layer.

FIG. 3C shows an enlarged top view of the tip of a test strip with a dielectric-spacer layer and a reagent layer.

FIG. 4A shows an enlarged top view of the tip of a test strip with a first capillary with no surface modification prior to the application of a reagent layer.

FIG. 4B shows an enlarged top view of the tip of a test strip with a first capillary with surface modifications prior to the application of a reagent layer.

FIG. 4C shows an enlarged top view of the tip of a test strip with a first capillary with no surface modifications prior to the application of a reagent layer.

FIG. 4D shows an enlarged top view of the tip of a test strip with a first capillary with surface modifications prior to the application of a reagent layer

DESCRIPTION OF THE EMBODIMENTS

Figure 1B:
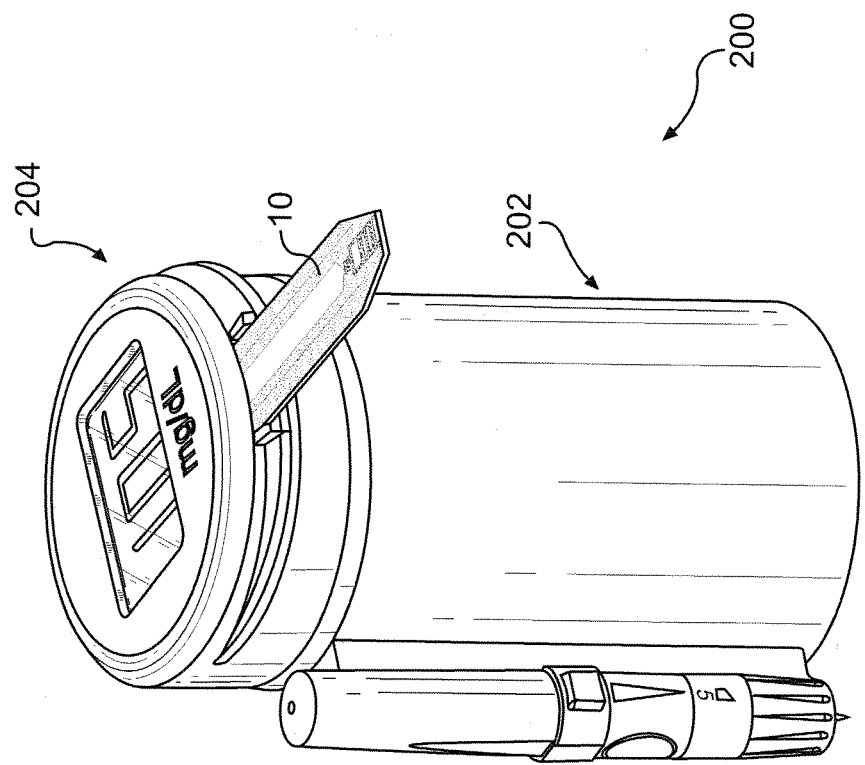
FIG. 1B illustrates a test meter that can be used with test media produced according to the methods of the present disclosure.

Reference will now be made in detail to the exemplary embodiments of the invention, examples of which are illustrated in the accompanying drawings. Wherever possible, the same reference numbers will be used throughout the drawings to refer to the same or like parts.

In accordance with an exemplary embodiment, a biosensor manufacturing method is described. Many industries have a commercial need to monitor the concentration of particular constituents in a fluid. The oil refining industry, wineries, and the dairy industry are examples of industries where fluid testing is routine. In the health care field, people such as diabetics, for example, need to monitor various constituents within their bodily fluids using biosensors. A number of systems are available that allow people to test a body fluid (e.g. blood, urine, or saliva), to conveniently monitor the level of a particular fluid constituent, such as, for example, cholesterol, proteins or glucose.

For purposes of this disclosure, "distal" refers to the portion of a test strip further from the fluid source (i.e. closer to the meter) during normal use, and "proximal" refers to the portion closer to the fluid source (e.g. a finger tip with a drop of blood for a glucose test strip) during normal use. The test strip may include a plurality of sample chambers for receiving a user's fluid sample, such as, for example, a blood sample. The sample chambers and test strip of the present specification can be formed using materials and methods described in commonly owned U.S. Pat. No. 6,743,635, which is hereby incorporated by reference in its entirety. Accordingly, a sample chamber may include a first opening in the proximal end of the test strip and a second opening for venting the sample chamber. Each sample chamber may be dimensioned so as to be able to draw the blood sample in through the first opening and to hold the blood sample in the sample chamber by capillary action. The test strip can include a tapered section that is narrowest at the proximal end, or can include other indicia in order to make it easier for the user to locate the first opening and apply the blood sample.

A first set of electrodes, such as a working electrode and a counter (or in an exemplary embodiment, proximal) electrode, can be disposed in a first sample chamber optionally along with one or more fill-detect electrodes. A reagent layer is disposed in the first sample chamber and preferably contacts at least the working electrode. The reagent layer may include an enzyme, such as glucose oxidase or glucose dehydrogenase, and a mediator, such as potassium ferricyanide or ruthenium hexamine. The first sample chamber may be configured to permit determination of one or more analytes in a blood sample, such as, for example, glucose. A second set of electrodes may be disposed in a second sample chamber, such as, for example, a proximal electrode and a distal electrode. The electrodes may be spaced at a predetermined distance such that hematocrit may be determined by measurement of electrical impedance between the two electrodes in the second sample chamber.

The test strip has, near its distal end, a plurality of electrical contacts that are electrically connected to the electrodes via conductive traces. In addition, the test strip may also include a second plurality of electrical strip contacts near the distal end of the strip. The second plurality of electrical contacts can be arranged such that they provide, when the strip is inserted into the meter, a distinctly discernable lot code readable by the meter. In some embodiments, the electrical contacts may be at least partially covered with an at least partially conductive material to improve the wear properties of the electrical contacts.

An individual test strip may also include an embedded code relating to data associated with a lot of test strips, or data particular to that individual strip. The embedded information presents data readable by the meter signaling the meter's microprocessor to access and utilize a specific set of stored calibration parameters particular to test strips from a manufacturing lot to which the individual strip belongs, or to an individual test strip. The system may also include a check strip that the user may insert into the meter to check that the instrument is electrically calibrated and functioning properly. The readable code can be read as a signal to access data, such as calibration coefficients, from an on-board memory unit in the meter.

In order to save power, the meter may be battery powered and may stay in a low-power sleep mode when not in use. When the test strip is inserted into the meter, one or more electrical contacts on the test strip form electrical connections with one or more corresponding electrical contacts in the meter. The second plurality of electrical contacts may bridge a pair of electrical contacts in the meter, causing a current to flow through a portion of the second plurality of electrical contacts. The current flow through the second plurality of electrical contacts causes the meter to wake up and enter an active mode. The meter also reads the code information provided by the second plurality and can then identify, for example, the particular test to be performed or a confirmation of proper operating status. Calibration data pertaining to the strip lot, for either the analyte test or the hematocrit test, discussed below, can also be encoded or otherwise represented. In addition, based on the particular code information, the meter can also identify the inserted strip as either a test strip or a check strip. If the meter detects a check strip, it performs a check strip sequence. If the meter detects a test strip, it performs a test strip sequence.

In the test strip sequence, the meter validates the working electrode, counter electrode, and, if included, the fill-detect electrodes, by confirming that there are no low-impedance paths between any of these electrodes. If the electrodes are valid, the meter indicates to the user that a sample may be applied to the test strip. The meter then applies a drop-detect voltage between any two suitable electrodes and detects a fluid sample, such as, a blood sample, by detecting a current flow between the working and proximal electrodes (i.e., a current flow through the blood sample as it bridges the working and proximal electrodes). To detect that an adequate sample is present in the sample chamber, and that the blood sample has traversed the reagent layer and mixed with the chemical constituents in the reagent layer, the meter may apply a fill-detect voltage to the one or more fill-detect electrodes and measure any resulting current flow. If a resulting electrical property reaches a sufficient level within a predetermined period of time, the meter indicates to the user that adequate sample is present and has mixed with the reagent layer.

The meter can be programmed to wait for a predetermined period of time after initially detecting the blood sample to allow the blood sample to react with the reagent layer. Alternatively, the meter may be configured to immediately begin taking readings in sequence. During an exemplary fluid measurement sequence using amperometry, the meter applies an assay voltage between the working and proximal electrodes and takes one or more measurements of the resulting current flowing between the working and counter electrodes. The assay voltage is near the redox potential of the chemistry in the reagent layer, and the resulting current is related to the concentration of the particular constituent measured, such as, for example, the glucose level in a blood sample. Voltammetry and coulometry approaches, as known in the art, could also be employed.

In one example, the reagent layer may react with glucose in the blood sample in order to determine the particular glucose concentration. In one example, glucose oxidase or glucose dehydrogenase is used in the reagent layer. During a sample test, the glucose oxidase initiates a reaction that oxidizes the glucose to gluconic acid and reduces a mediator such as ferricyanide or ruthenium hexamine. When an appropriate voltage is applied to a working electrode relative to a counter electrode, the ferrocyanide is oxidized to ferricyanide, thereby generating a current that is related to the glucose concentration in the blood sample.

The test strip may also include a second sample chamber configured to permit determination of hematocrit. The second sample chamber may include a reagent, such as a surfactant and/or a surface treatment, in order to prevent electrode fouling. The meter can determine hematocrit by measuring the impedance of the blood sample in the second sample chamber by applying an appropriate voltage and/or current and reading suitable measurements to calculate an impedance value. The calculated impedance value correlates with hematocrit, which can vary and can affect glucose determination. It is also contemplated that the second sample chamber may be configured to measure another analyte, such as, for example, blood ketones.

The meter can calculate the glucose level based on the measured current from the first sample chamber and, optionally, enhance that calculation based on the impedance value determined using the second sample chamber. This data along with other calibration data contained within the test strip may permit the meter to determine a glucose level and display the calculated glucose level to the user.

Electrodes positioned within the sample chamber may include a working electrode, a counter electrode, a fill-detect electrode, a proximal electrode, and a distal electrode. A reagent layer can be disposed in the first sample chamber and may cover at least a portion of the working electrode, which can also be disposed at least partially in the sample chamber. The reagent layer can include, for example, an enzyme, such as glucose oxidase or glucose dehydrogenase, and a mediator, such as potassium ferricyanide or ruthenium hexamine, to facilitate the detection of glucose in blood. It is contemplated that other reagents and/or other mediators can be used to facilitate detection of glucose and other constituents in blood and other body fluids. The reagent layer can also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485).

As mentioned previously, biosensors may inaccurately measure a particular constituent level in blood due to unwanted effects of certain blood components on the method of measurement. For example, the hematocrit level (i.e. the percentage of blood occupied by red blood cells) in blood can erroneously affect a resulting analyte concentration measurement. Thus, it may be desirable to apply chemical additives and/or signal processing techniques as previously described, to reduce the sensitivity of the blood sample to hematocrit. Further, it may be desirable to separately measure hematocrit of a blood sample such that any analyte measurement can be adjusted to correct for hematocrit variations. In accordance with an exemplary embodiment of the present invention, a blood sample may be divided into at least two different regions on a biosensor and tested separately. For example, a blood sample may be diverted into a first sample chamber to undergo an electrochemical test, as described above, to determine, for example, the concentration of glucose within the sample. The blood sample may also be diverted into a second sample chamber to undergo a separate test, as discussed in detail below, to determine the hematocrit level of the blood sample. It is also contemplated that a third sample chamber may be used to perform another determination, such as, for example, a determination of blood sample temperature, a concentration of a second analyte, a second measurement of the first analyte concentration, and/or an on board control to perform a calibration step. In some embodiments, the second sample chamber may be configured to perform one or more determinations as described for the third sample chamber.

In some embodiments, first and second sample chambers can be dimensioned and configured to draw a blood sample into the sample chambers via capillary action. Each sample chamber may also include one or more electrodes positioned within the sample chambers and configured to contact the blood sample. The first sample chamber may include reagents and electrodes configured to determine a blood glucose concentration. Hematocrit may be measured using the second sample chamber. For example, the second chamber may include a set of electrodes spaced apart at a predetermined distance, and hematocrit may be determined by measuring an impedance of the blood sample between the electrodes. The distance between the electrodes in the second sample chamber can be optimized for measuring hematocrit while the electrodes of the first sample chamber may be configured for glucose determination.

Hematocrit may be determined using any methods known in the art. For example, hematocrit may use electrical, optical, chemical, or any other suitable method. Optical methods may include reflective or transmission techniques. Electrical methods may include amperometric, voltametric, or coulometric. In some embodiments, hematocrit may be determined using an AC excitation, wherein an impedance measurement may be obtained using digital signal processing, analog processing, or similar suitable technique.

To determine impedance, an AC signal can be applied across a set of electrodes in the second sample chamber. Impedance may include real or complex values, wherein effective, reactive, capacitive and/or resistive parameters may be associated with hematocrit. As explained by the Coulter principle, blood hematocrit can be derived from an impedance measurement obtained by applying an AC signal to the blood sample. More specifically, impedance $Z_R$ can be measured from the blood sample by dividing the phasor voltage $V_R$ applied across the electrodes and dividing this value by the phasor current $I_R$ passing through the electrodes and the blood sample. Thus, the impedance of the blood sample is:

$$Z_R = \frac{V_r}{I_r}$$

Following impedance measurement, hematocrit can be determined by applying the measured impedance value or multiple values at several different frequencies of excitation to an equation, an algorithm, a look-up chart, or any other suitable method. For example, an algorithm may correlate a glucose level with an electrical measurement value up to a threshold value, and above that threshold, a correction value correlated with hematocrit may be applied to any glucose determination. Once the value correlated to the hematocrit level within the blood sample is determined, the value may be used to modify the calculated glucose concentration such that an enhanced or corrected value of the concentration of glucose of the blood sample can be determined. Determining a glucose measurement and/or a hematocrit value may also require incorporating of one or more correction values, such as, for example, for variations in a temperature of a blood sample.

In accordance with another exemplary embodiment of the present invention, a test strip may further comprise a third sample chamber configured to permit determination of a third parameter associated with a blood sample. The third parameter to be measured may be selected from a group consisting of a temperature, a concentration of a second analyte, and an on-board control, as described in detail below.

In some embodiments, one or more sample chambers may be configured to receive a control solution. The control solution may be used to periodically test one or more functions of a meter. For example, a control solution may include a solution of known electrical properties and an electrical measurement of the solution may be performed by the meter. When the meter detects the use of a control solution, it can provide an operational check of both sample chambers functionality to verify the systems measurement integrity. The meter readout may then be compared to the known glucose value of the solution to confirm that the meter is functioning to an appropriate accuracy. Any measurement of a control solution may be performed using one or more electrodes of the second sample chamber. In addition, data associated with a measurement of a control solution may be processed, stored and/or displayed using a meter differently to any data associated with a glucose measurement. Such different treatment of data associated with the control solution may permit a meter, or user, to distinguish a glucose measurement, or may permit exclusion of any control measurements when conducting any statistical analysis of glucose measurements.

Figure 1A:
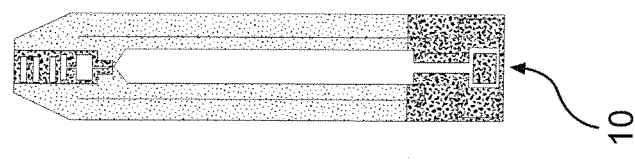
FIG. 1A illustrates test media that can be produced using the methods of the present disclosure.
Figure 1C:
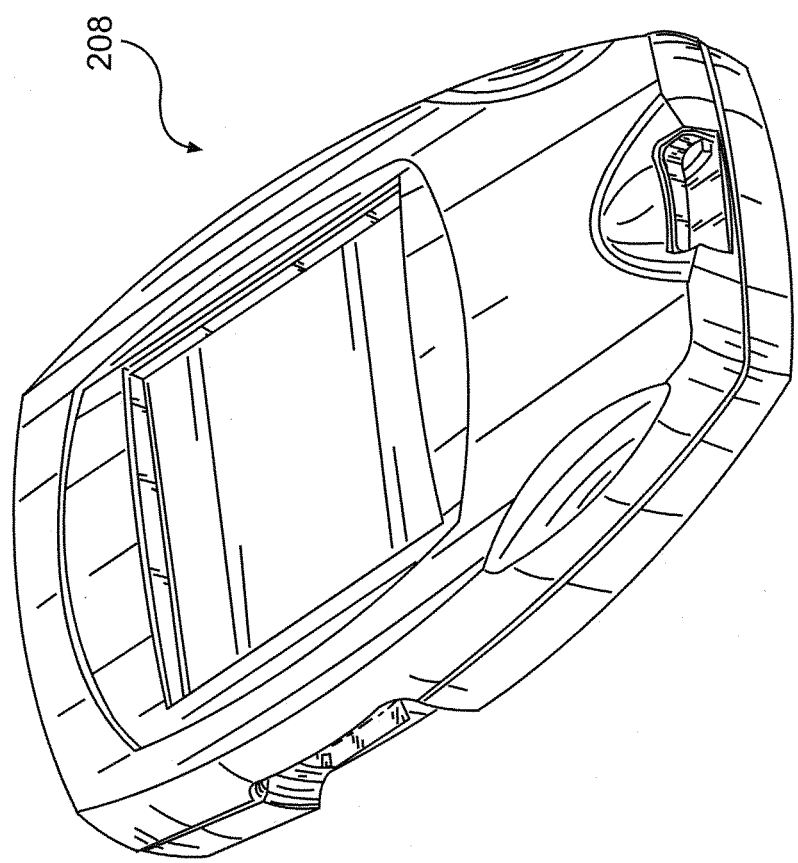
FIG. 1C illustrates a test meter that can be used with test media produced according to the methods of the present disclosure.

The present disclosure provides a method for producing a diagnostic test strip 10, as shown in FIG. 1A. Test strip 10 of the present disclosure may be used with a suitable test meter 200, 208, as shown in FIGS. 1B and 1C, to detect or measure the concentration of one or more analytes. As shown in FIG. 1A, test strip 10 is planar and elongated in design. Test strip 10, however, may be provided in any suitable form including, for example, ribbons, tubes, tabs, discs, or any other suitable form. Furthermore, test strip 10 can be configured for use with a variety of suitable testing modalities, including electrochemical tests, photochemical tests, electro-chemiluminescent tests, and/or any other suitable testing modality.

Test meter 200, 208 may be selected from a variety of suitable test meter types. For example, as shown in FIG. 1B, test meter 200 includes a vial 202 configured to store one or more test strips 10. The operative components of test meter 200 may be contained in a meter cap 204. Meter cap 204 may contain electrical meter components, can be packaged with test meter 200, and can be configured to close and/or seal vial 202. Alternatively, a test meter 208 can include a monitor unit separated from storage vial, as shown in FIG. 1C. Any suitable test meter may be selected to provide a diagnostic test using test strip 10 produced according to the disclosed methods.

Test Strip Configuration

Figure 2A:
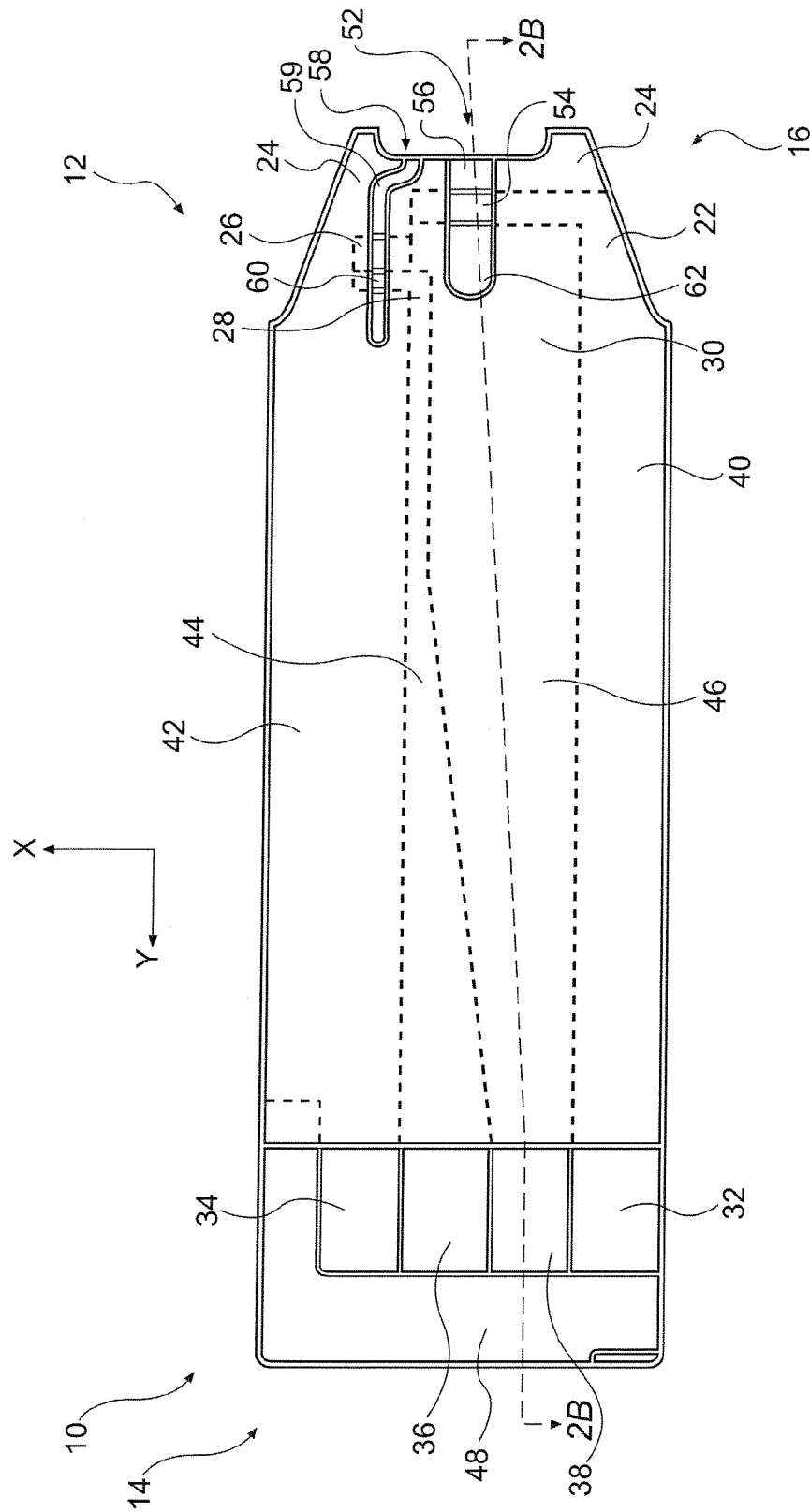
FIG. 2A is a top plan view of a test strip according to an exemplary embodiment of the invention.
Figure 2B:
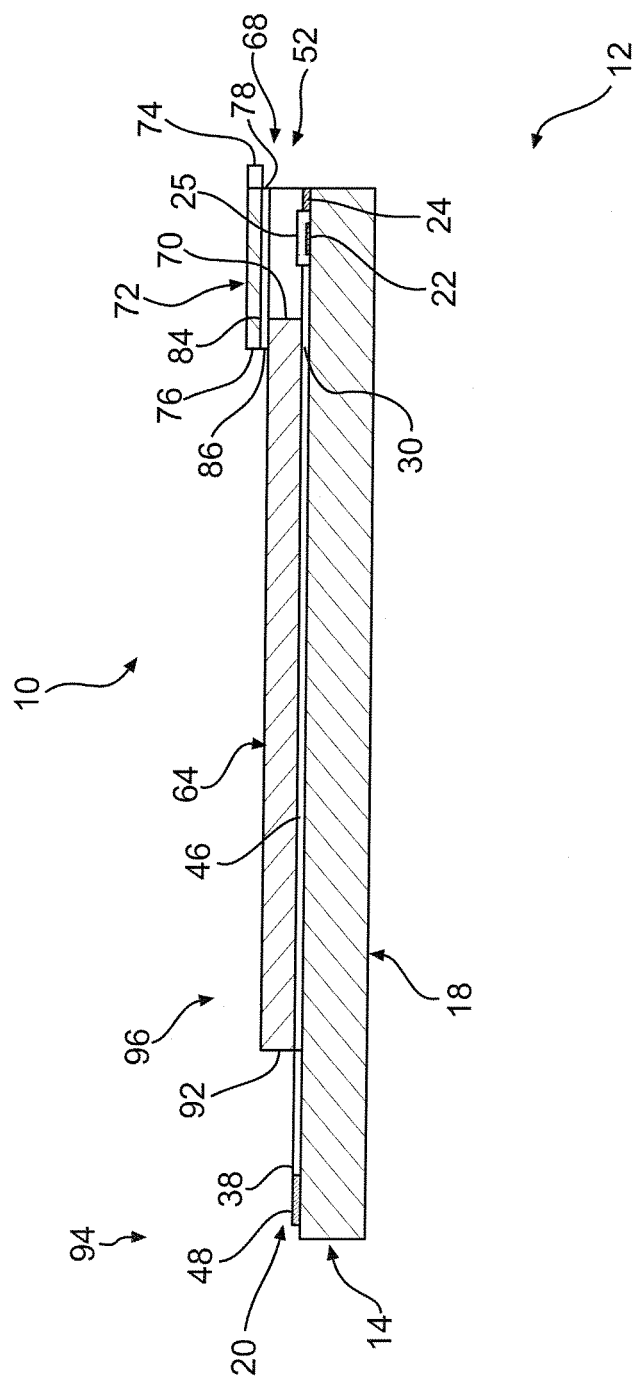
FIG. 2B is a cross-sectional view of the test strip of FIG. 2A, taken along line 2B-2B.

With reference to the drawings, FIGS. 2A and 2B show a test strip 10, in accordance with an exemplary embodiment of the present invention. Test strip 10 preferably takes the form of a generally flat strip that extends from a proximal end 12 to a distal end 14. Preferably, test strip 10 is sized for easy handling. For example, test strip 10 can measure approximately 35 mm long (i.e., from proximal end 12 to distal end 14) and approximately 9 mm wide. The strip, however, can be any convenient length and width. For example, a meter with automated test strip handling may utilize a test strip smaller than 9 mm wide. Additionally, proximal end 12 can be narrower than distal end 14 in order to provide facile visual recognition of the distal end. Thus, test strip 10 can include a tapered section 16, in which the full width of test strip 10 tapers down to proximal end 12, making proximal end 12 narrower than distal end 14. As described in more detail below, the user applies the blood sample to an opening in proximal end 12 of test strip 10. Thus, providing tapered section 16 in test strip 10, and making proximal end 12 narrower than distal end 14, assists the user in locating the opening where the blood sample is to be applied. Further, other visual means, such as indicia, notches, contours or the like are possible.

As shown in FIG. 2B, test strip 10 can have a generally layered construction. Working upwardly from the bottom layer, test strip 10 can include a base layer 18 extending along the entire length of test strip 10. Base layer 18 can be formed from an electrically insulating material and has a thickness sufficient to provide structural support to test strip 10. For example, base layer 18 can be a polyester material about 0.35 mm thick.

According to the illustrative embodiment, a conductive layer 20 is disposed on base layer 18. Conductive layer 20 includes a plurality of electrodes disposed on base layer 18 near proximal end 12, a plurality of electrical contacts disposed on base layer 18 near distal end 14, and a plurality of conductive regions electrically connecting the electrodes to the electrical contacts. In the illustrative embodiment depicted in FIG. 2A, the plurality of electrodes includes a working electrode 22, a proximal (or counting) electrode 24, a distal electrode 28, and a fill-detect electrode 30.

Defined between proximal electrode 24 and distal electrode 28 is an electrically isolated region 26, wherein the distance between electrodes 24 and 28 may be about 1 mm. The electrical contacts can correspondingly include a working electrode contact 32, a proximal electrode contact 34, a distal electrode contact 36, and a fill-detect electrode contact 38. The conductive regions can include a working electrode conductive region 40, electrically connecting working electrode 22 to working electrode contact 32, a proximal electrode conductive region 42, electrically connecting proximal electrode 24 to proximal electrode contact 36, a distal electrode conductive region 44 electrically connecting distal electrode 28 to distal electrode contact 36, and a fill-detect electrode conductive region 46 electrically connecting fill-detect electrode 30 to fill-detect contact 38. Further, the illustrative embodiment is depicted with conductive layer 20 including an auto-on conductor 48 disposed on base layer 18 near distal end 14.

In addition, the present disclosure provides test strips 10 that include electrical contacts that are resistant to scratching or abrasion. Such test strips 10 can include conductive electrical contacts formed of two or more layers of conductive and/or semi-conductive material. A first lower conductive layer 20 can include a conductive metal, ink, or paste. A second upper layer (not illustrated) can include a conductive ink or paste. Further, in some embodiments, the upper layer can have a resistance to abrasion that is greater than the lower layer. In addition, the second upper layer may have a thickness such that, even when scratched or abraded, the entire thickness of the conductive layer will not be removed, and the electrical contact will continue to function properly. Thus, such test strips 10 can include electrical contacts having material properties and dimensions such that, even when scratched or abraded, the test strips will continue to function properly. Further information relating to electrical contacts that are resistant to scratching or abrasion are described in U.S. patent application Ser. No. 11/458,298 which is incorporated by reference herein in its entirety.

The next layer in the illustrative test strip 10 is a dielectric-spacer layer 64 disposed on conductive layer 20. Dielectric-spacer layer 64 is composed of an electrically insulating material, such as polyester. Dielectric-spacer layer 64 can be about 0.100 mm thick and covers portions of working electrode 22, a proximal electrode 24, a distal electrode 28, a fill-detect electrode 30, and conductive regions 40-46, but in the illustrative embodiment does not cover electrical contacts 32-38 or auto-on conductor 48. For example, dielectric-spacer layer 64 can cover substantially all of conductive layer 20 thereon, from a line just proximal of contacts 32 and 34 all the way to proximal end 12, except for a first sample chamber 52 and a second sample chamber 58 extending from proximal end 12. In this way, first sample chamber 52 can define an exposed portion 54 of working electrode 22, an exposed portion 56 of proximal electrode 24, and an exposed portion 62 of fill-detect electrode 30. Second sample chamber 58 can define an exposed portion 59 of proximal electrode 24 and an exposed portion 60 of distal electrode 28. In some embodiments, first sample chamber 52 may be configured to detect an analyte concentration in a blood sample and second sample chamber 58 may be configured to determine a hematocrit of the blood sample. The shape of sample chambers 52 and 58 may be achieved prior to application on the base layer. Alternatively sample chambers 52 and 58 may be formed subsequently, which may allow for tighter tolerances to be achieved in the formation of the sample chambers 52 and 58.

A cover 72, having a proximal end 74 and a distal end 76, can be attached to dielectric-spacer layer 64 via an adhesive layer 78. Cover 72 can be composed of an electrically insulating material, such as polyester, and can have a thickness of about 0.1 mm. Additionally, the cover 72 can be transparent.

Adhesive layer 78 can include a polyacrylic or other adhesive and have a thickness of about 0.013 mm. Adhesive layer 78 can consist of sections disposed on spacer 64 on opposite sides of first sample chamber 52. A break 84 in adhesive layer 78 extends from distal end 70 of first sample chamber 52 to an opening 86. Cover 72 can be disposed on adhesive layer 78 such that its proximal end 74 is aligned with proximal end 12 and its distal end 76 is aligned with opening 86. In this way, cover 72 covers first sample chamber 52 and break 84. It is also contemplated that cover 72 may similarly cover second sample chamber 58.

Proximal end 74 of cover 72 can extend from distal end 70 beyond proximal end 12 to create an overhang, as shown in FIG. 2B. The overhang may be formed by extending cover 72 beyond proximal end 12 and/or by removing at least part of base layer 18 or other appropriate material under cover 72 to create a notch or similar structure. This overhang/notch configuration can aid in forming a hanging reservoir for a blood sample, via surface tension, to aid in providing a sufficient sample into first sample chamber 52 and second sample chamber 58. It is also contemplated that various materials, surface coatings (e.g. hydrophilic and/or hydrophobic), or other structure protrusions and/or indentations at proximal end 12 may be used to form a suitable blood sample reservoir.

First sample chamber 52 and second sample chamber 58 may be configured to receive separate portions of a blood sample applied to test strip 10. Proximal end 68 of first sample chamber 52 defines a first opening in first sample chamber 52, through which the blood sample is introduced into first sample chamber 52. At distal end 70 of first sample chamber 52, break 84 defines a second opening in first sample chamber 52, for venting first sample chamber 52 as a fluid sample enters first sample chamber 52. First sample chamber 52 is dimensioned such that a blood sample applied to its proximal end 68 is drawn into first sample chamber 52 by capillary action, with break 84 venting first sample chamber 52 through opening 86, as the blood sample enters. Moreover, first sample chamber 52 can advantageously be dimensioned so that the blood sample that enters first sample chamber 52 by capillary action is about 1 micro-liter or less. For example, first sample chamber 52 can have a length (i.e., from proximal end 12 to distal end 70) of about 0.140 inches, a width of about 0.060 inches, and a height (which can be substantially defined by the thickness of dielectric-spacer layer 64) of about 0.005 inches. Other dimensions could be used, however.

Proximal end 12 of second sample chamber 58 defines a first opening in second sample chamber 58, through which the blood sample is introduced into second sample chamber 58. Second sample chamber 58 is dimensioned such that a blood sample applied to its proximal end is drawn into second sample chamber 58 by capillary action. Additionally, second sample chamber 58 can advantageously be dimensioned so that the blood sample that enters second sample chamber 58 by capillary action is about 0.5 micro-liters or less.

In some embodiments, a secondary sample chamber may be configured for operation with a continuous glucose monitoring system (not shown). Such a system may include systems and/or devices configured to automatically monitor a patient's glucose level. Such systems may periodically sample body fluid containing cellular or biological matter that may affect a glucose determination. Such systems may also benefit by using a secondary sample chamber configured to determine hematocrit, or a similar measurement, using one of more of the methods described here.

As shown in FIG. 2B, a reagent layer 25 is disposed in first sample chamber 52, wherein reagent layer 25 may include one or more chemical constituents to enable the level of glucose in the blood sample to be determined electrochemically. Thus, reagent layer 25 may include an enzyme specific for glucose and a mediator, as described above. In addition, reagent layer 25 may also include other components, buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485).

As depicted in FIG. 2B, the arrangement of the various layers in illustrative test strip 10 can result in test strip 10 having different thicknesses in different sections. In particular, among the layers above base layer 18, much of the thickness of test strip 10 can come from the thickness of spacer 64. Thus, the edge of spacer 64 that is closest to distal end 14 can define a shoulder 92 in test strip 10. Shoulder 92 can define a thin section 94 of test strip 10, extending between shoulder 92 and distal end 14, and a thick section 96, extending between shoulder 92 and proximal end 12. The elements of test strip 10 used to electrically connect it to the meter, namely, electrical contacts 32-38 and auto-on conductor 48, can all be located in thin section 94. Accordingly, the connector in the meter can be sized and configured to receive thin section 94 but not thick section 96, as described in more detail below. This can beneficially cue the user to insert the correct end, i.e., distal end 14 in thin section 94, and can prevent the user from inserting the wrong end, i.e., proximal end 12 in thick section 96, into the meter. Although FIGS. 2A and 2B illustrate an illustrative embodiment of test strip 10, other configurations, chemical compositions and electrode arrangements could be used.

As depicted in FIG. 2A fill-detect electrode 30 can function with working electrode 22 to perform a fill-detect feature, as previously described. Further, working electrode 22 may operate in conjunction with proximal electrode 24 to detection of a constituent of a sample in first sample chamber 52, as described above. Other configurations of electrodes on test strip 10 are possible, such as, for example, multiple fill-detect electrodes and multiple working electrodes.

As depicted in the FIG. 2B, fill-detect electrode 30 is advantageously located on the distal side of reagent layer 25. In this arrangement, the sample introduced into first sample chamber 52 will have traversed reagent layer 25 before reaching fill-detect electrode 30. This arrangement beneficially allows the fill-detect electrode 30 to indicate not only whether sufficient blood sample is present in first sample chamber 52, but also when, concomitantly, the blood sample has sufficiently mixed with the chemical constituents of reagent layer 25.

Sacrificial Spacer Layer

One method to reproducibly dispense a reagent within a particular sample chamber involves the use of sacrificial-spacer layer 31. In this method, a thin film (1-4 mils) is punched in the desired pattern of the chemistry layer and laminated onto the substrate. Thus, sacrificial-spacer layer 31 covers at least the tapered section 16 of the test strip 10 where the sample chambers will be formed except for a predefined area of at least one sample chamber where deposition of reagent layer 25 is desired. The layer adheres to the substrate well enough to contain the chemistry solution dispensed into it, but is readily delaminated from the substrate once the chemistry is dried. An example of a material that can be used as sacrificial-spacer layer 31 is Kapton® tape. To complete the formation of the sample chambers the dielectric-spacer layer 64 is laminated. Sensors assembled using this procedure showed performance comparable to standard sensors with the chemistry dispensed directly into the well (75 mg/dL glucose: 2450 nA, 2.4% CV, 550 mg/dL glucose: 12700 nA, 7.5% CV).

It is contemplated that a sacrificial spacer layer may also be used for precise chemistry patterning for a single well sensor. A sacrificial spacer layer in a single well sensor may allow for a thinner, dispensable chemistry without the chemistry experiencing physical interactions with the walls of the sample cavity (i.e., creating a meniscus bulge).

As shown in FIG. 3A, sacrificial-spacer layer 31 with preformed pattern 29 is applied to tapered section 16 of test strip 10. After application of sacrificial-spacer layer 31 onto test strip 10, reagent layer 25 is applied within preformed pattern 29. Once reagent layer 25 has sufficiently dried, sacrificial-spacer layer 31 can be removed as shown in FIG. 3B such that test strip 10 now includes reagent layer 25 resembling the shape of preformed pattern 29. Next, FIG. 3C illustrates how dielectric-spacer layer 64 is applied to test strip 10 to define first capillary 27, which contains reagent layer 25.

Surface Modifications

When the amount of the surfactant in the chemistry solution of reagent layer 25 is reduced to minimize spreading into the other sample chambers, reagent layer 25 does not dry uniformly, which translates into poor precision of the measurement caused by poor uniformity of reagent layer 25. Another method to reproducibly dispense a reagent within a particular sample chamber, however, involves using surface treatments on the area where reagent layer 25 is to be applied while masking the other portions within tapered section 16 of test strip 10. For example, the sample chamber where reagent layer 25 will be deposited can be treated with oxygen plasma or with a hydrophilic thiol monolayer solution, such as, for example, sodium 2-mercaptoethanesulfonate, while other sample chambers are masked to protect them from the surface treatment. The other sample chambers may be masked with, for example, Kapton® tape. As a result of treating a sample chamber with oxygen plasma or with a hydrophilic thiol monolayer solution, reagent layer 25 spreads readily and forms a uniform coating within the sample chamber, even with reduced levels of surfactant within reagent layer 25.

For example, as depicted in FIG. 4A, first capillary 27 of test strip 10 has not had any surface modifications. As a result, deposition of reagent layer 25 in capillary 27 may result in having reagent layer 25 only cover or fill one portion of first capillary 27. In FIG. 4B, however, first capillary 27 has received surface modifications resulting in a more even distribution of reagent layer 25 throughout first capillary 27. In another example, FIG. 4C illustrates first capillary 27 with an alternative geometry without surface modifications. Without surface modifications, deposition of reagent layer 25 into first capillary 27 of FIG. 4C results in uneven or sporadic distribution of reagent layer 25 within first capillary 27. Alternatively, FIG. 4D depicts first capillary 27 with surface modifications, and thus, reagent layer 25 is more evenly distributed within first capillary 27.

Chemical Dam

Another method to reproducibly dispense reagent layer 25 within a particular sample chamber involves the use of chemical dam 37. When dispensing reagent layer 25 within a sample chamber of a test strip 10, it is desirable to dispense a sufficient amount to fill the entire sample chamber. Filling the entire sample chamber however, may result in reagent layer 25 spreading outside of a sample chamber. Reagent layer 25, however, can be contained within a sample well by using chemical dam 37 that is applied at an entrance to the sample chamber and then cured to become solid. Chemical dam 37 may be comprised of, for example, a PVA-based adhesive for easy dispensing the desired location. Following the curing process, this adhesive is solid and functions as a dam during chemistry application.

After reagent layer 25 has been dispensed and dried, chemical dam 37 can be removed, for example, by introducing a slight bend in the substrate at or near chemical dam 37. Further, a liner may be applied between the substrate and chemical dam 37 such that the chemical dam can be removed by pulling on an exposed end of the liner to remove the liner and chemical dam 37 from the substrate.

Figure 5A:
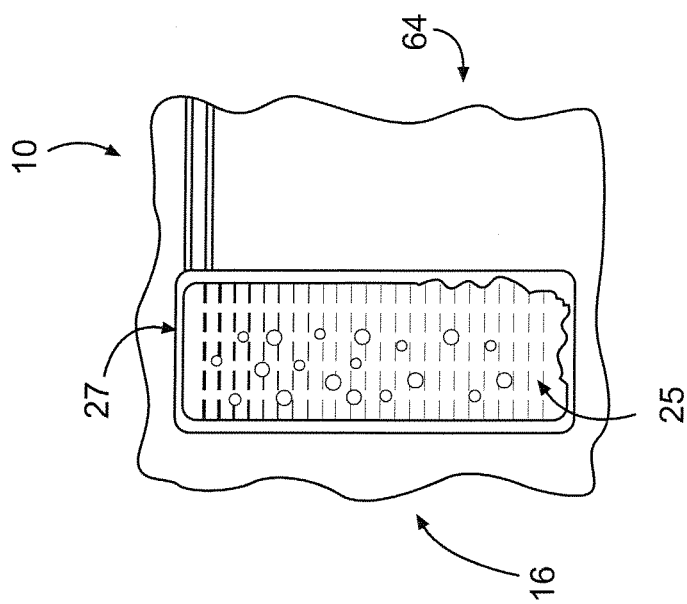
FIG. 5A shows an enlarged top view of the tip of a test strip with a first capillary with a chemical dam.
Figure 5B:
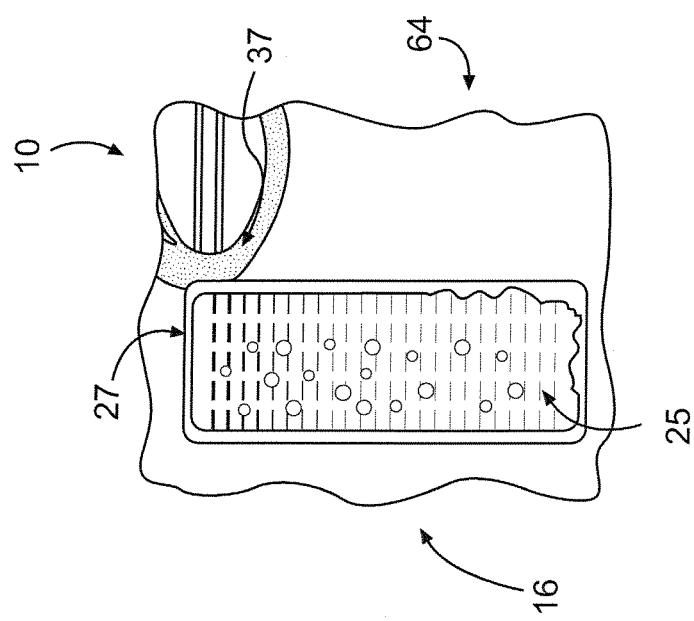
FIG. 5B shows an enlarged top view of the tip of a test strip with a first capillary with the chemical dam of 5A removed.

FIG. 5A shows tapered section 16 of the test strip 10 with first capillary 27. Further capillary 27 of FIG. 5A. is isolated from other capillaries of test strip 10 by chemical dam 37. Therefore, reagent layer 25 can be dispensed within first capillary 27 without reagent layer 25 migrating outside of first capillary 27. Further, FIG. 5B illustrates that chemical dam 37 cam be removed after reagent layer 25 has been dispensed an dried, and therefore, allowing a sample to enter first capillary 27.

Spacer Dam

In this method, reagent layer 25 can be reproducibly dispensed within a particular sample chamber by isolating a sample chamber with spacer dam 35. Spacer dam 35, which may be comprised of PET film, for example, is ideally applied prior to dispensing reagent layer 25 and material is removed once reagent layer 25 is dried. Removal of spacer dam 35 can be achieved, for example, by using laser ablation. In particular, laser ablation of spacer dam 35 may be achieved by a 532 nm AVIA laser. A number of other methods can be used for removal of spacer dam 35 such as, for example, chemical etching, mechanical removal (ex: rotary blade), and heat embossing.

Figure 6A:
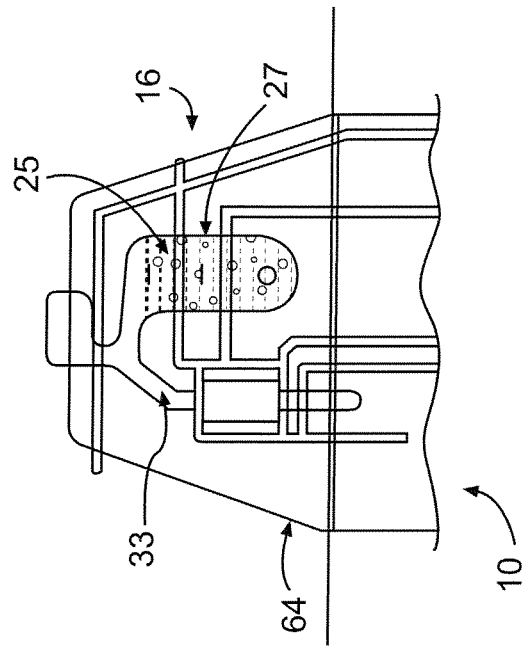
FIG. 6A shows an enlarged top view of the tip of a test strip with a first capillary with a spacer dam.
Figure 6B:
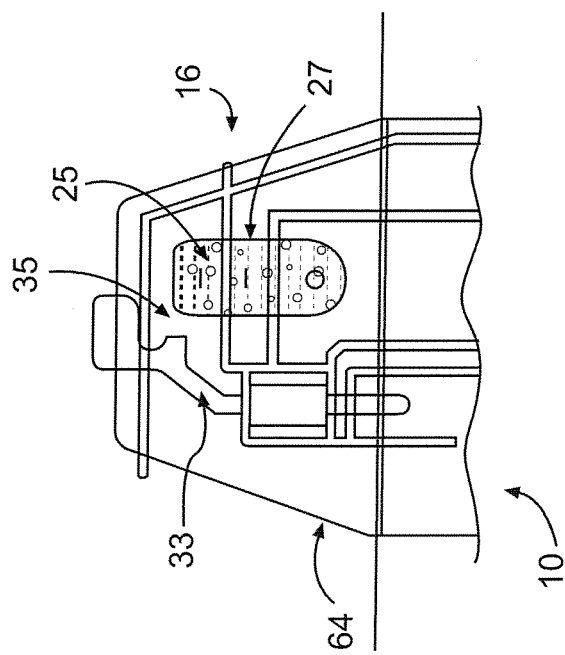
FIG. 6B shows an enlarged top view of the tip of a test strip with a first capillary with the spacer dam of 6A removed.

FIG. 6A illustrates reagent layer 25 within first capillary 27. Further, spacer dam 35 isolates first capillary 27 from second capillary 33, such that reagent layer 25 cannot migrate during the dispensing and drying process from first capillary 27 to second capillary 33. Once reagent layer 25 has been adequately dried, spacer dam 35 can be removed, as illustrated in FIG. 6B, allowing a sample to enter first capillary 27.

Test Strip Array Configuration

Test strips can be manufactured by forming a plurality of strips in an array along a reel or web of substrate material. The term "reel" or "web" as used herein applies to continuous webs of indeterminate length, or to sheets of determinate length. The individual strips, after being formed, can be separated during later stages of manufacturing. An illustrative embodiment of a batch process of this type is described infra. First, an illustrative test strip array configuration is described.

Figure 7B:
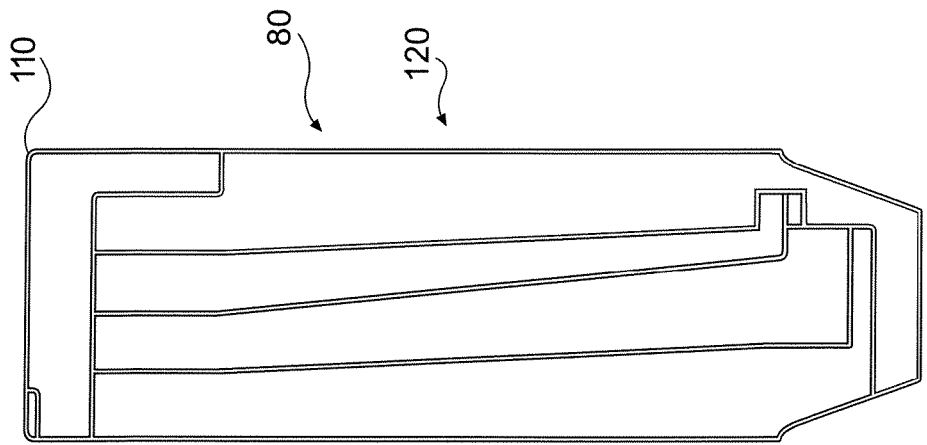
FIG. 7B is an enlarged tip view of a feature set on the reel of FIG. 7A.
Figure 7A:
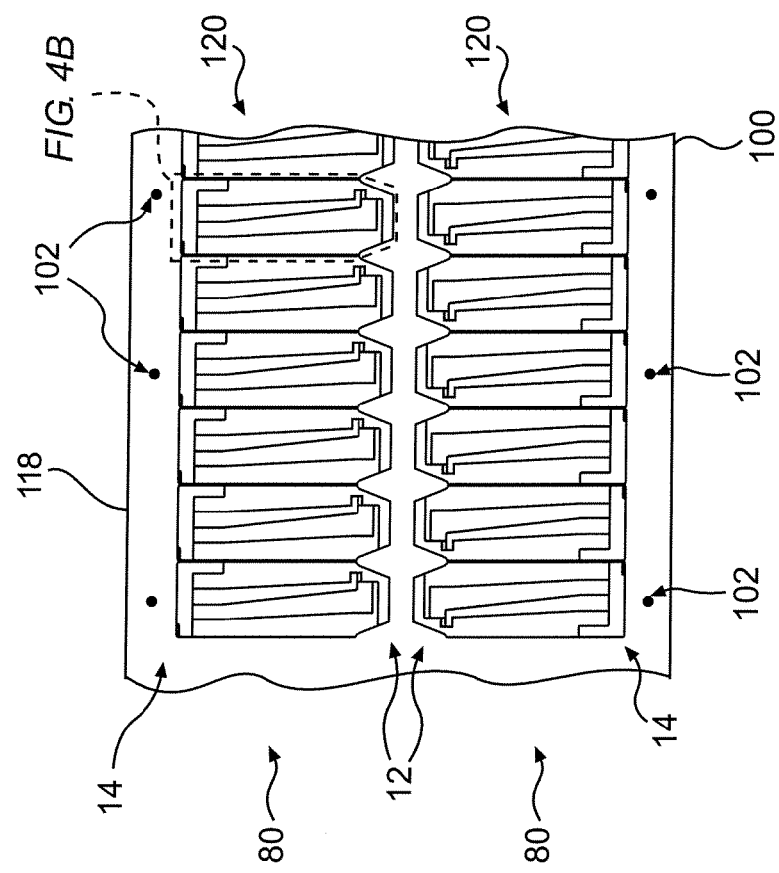
FIG. 7A is a top view of a reel according to an exemplary disclosed embodiment of the invention.

FIG. 7A shows a series of traces 80 formed in a substrate material coated with a conductive layer. Traces 80, formed in the exemplary embodiment by laser ablation, partially form the conductive layers of two rows of ten test strips as shown. In the exemplary embodiment depicted, proximal ends 12 of the two rows of test strips are in juxtaposition in the center of a reel 100. The distal ends 14 of the test strips are arranged at the periphery of reel 100. It is also contemplated that the proximal ends 12 and distal ends 14 of the test strips can be arranged in the center of reel 100. Alternatively, the two distal ends 14 of the test strips can be arranged in the center of reel 100. The lateral spacing of the test strips is designed to allow a single cut to separate two adjacent test strips. The separation of the test strip from reel 100 can electrically isolate one or more conductive components of the separated test strip 10.

As depicted in FIG. 7A, trace 80 for an individual test strip forms a plurality of conductive components; e.g., electrodes, conduction regions and electrode contacts. Trace 80 is comprised of individual cuts made by a laser following a specific trajectory, or vector. A vector can be linear or curvilinear, and define spaces between conductive components that are electrically isolating. Generally a vector is a continuous cut made by the laser beam.

The conductive components can be partially or entirely defined by ablated regions, or laser vectors, formed in the conductive layer. The vectors may only partially electrically isolate the conductive component, as the component can remain electrically connected to other components following laser ablation. The electrical isolation of the conductive components can be achieved following "singulation," when individual test strips are separated from reel or web 100. It is also contemplated that other conductive components may be electrically isolated during the laser ablation process. For example, fill detect electrodes may be isolated with the addition of one or more vectors.

FIG. 7A also includes registration points 102 at the distal end 14 of each test strip on reel 100. Registration points 102 assist the alignment of the layers during the lamination, punching and other manufacturing processes. It is further contemplated that registration points 102 may be located at locations other than the distal end 14 of each test strip trace 80 on reel 100. High quality manufacturing may require additional registration points 102 to ensure adequate alignment of laminate layers and/or other manufacturing processes, such as, for example, laser ablation of conductive components, reagent deposition, singulation, etc.

Figure 8:
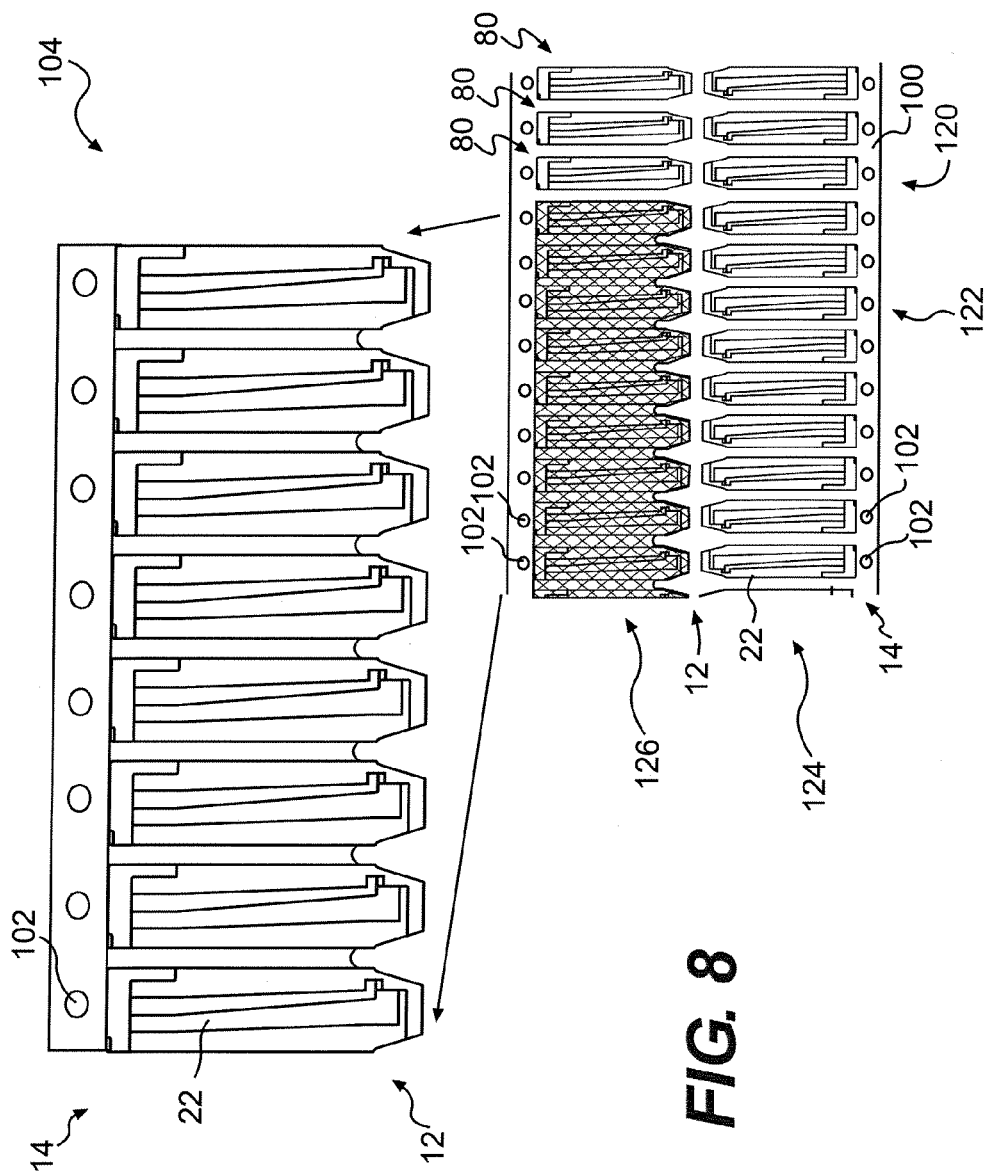
FIG. 8 is a top view of a test card according to a further illustrative embodiment of the invention.

FIG. 8 shows a "test card" 104 separated from reel 100. Test card 104 can contain a plurality of test strips 10 or traces 80, and a plurality of conductive components. In the preferred embodiment test card 104 can contain between 6 and 12 test strips 10 or traces 80. In other embodiments, test card 104 can contain a plurality of test strips 10 or traces 80. In the illustrated embodiment, test card 104 can include a lateral array of test strips 10 or traces 80. In other embodiments, test card 104 can include an array or arrays of test strips 10 or traces 80 in longitudinal and/or lateral configurations. It is further contemplated that test strips 10 or traces 80 may be in any arrangement on reel 100 suitable for manufacturing.

Test card 104 contains a plurality of conductive components. Some conductive components can be electrically isolated when the test card is removed from the reel. As shown in FIG. 8, working electrode 22 is electrically isolated. Other embodiments could include additional electrically isolated conductive components not shown in FIG. 8. It may be possible to analyze properties of the electrically isolated conductive components to assess the quality of the manufacturing process. The efficiency of the quality assessment process can be increased by testing at least one of the plurality of electrically isolated conductive components.

Batch Manufacturing of Test Strips

Test strip 10 may be manufactured using any suitable manufacturing methods. For example, one or more conductive components may be manufactured using laser ablation employing projected masks or raster scanning methods, screen printing, insert injection molding, and any other suitable techniques. One of more sample chambers, or capillaries, may be formed using a spacer, dielectric build-up, injection molded, laser ablation, or other suitable method. One illustrative embodiment for manufacturing test strip 10 will now be described in detail.

FIGS. 7A through 9 illustrate an exemplary method of manufacturing test strips. Although these figures shows steps for manufacturing test strip 10, as shown in FIGS. 7A through 9, it is to be understood that similar steps can be used to manufacture test strips having other configurations.

With reference to FIG. 7A, a plurality of test strips 10 can be produced by forming a structure 120 that includes a plurality of test strip traces 122 on reel 100. Test strip traces 122 include a plurality of traces 80, and can be arranged in an array that includes a plurality of rows. Each row 124 can include a plurality of test strip traces 122.

The separation process can also be used to electrically isolate conductive components of test strip 10. Laser ablation of the conductive layer may not electrically isolate certain conductive components. The non-isolated conductive components may be isolated by the separation process whereby test strips are separated from reel 100. The separation process may sever the electrical connection, isolating the conductive component. Separating test strip 10 can electrically isolate the counting electrode 24, fill detect-anode 28 and fill-detect cathode 30. The separation process can complete the electrical isolation of conductive components by selectively separating conductive components.

Further, the separation process can provide some or all of the shape of the perimeter of the test strips 10. For example, the tapered shape of tapered sections 16 of the test strips 10 can be formed during this punching process. Next, a slitting process can be used to separate the test strip structures 122 in each row 124 into individual test strips 10. The separation process may include stamping, slitting, scoring and breaking, or any suitable method to separate test strip 10 and/or card 104 from reel 100.

FIGS. 7A and 7B show only one test strip structure (either partially or completely fabricated), in order to illustrate various steps in a preferred method for forming the test strip structures 122. In this exemplary approach, the test strip structures 122 in integrated structure 120 are all formed on a sheet of material that serves as base layer 18 in the finished test strips 10. The other components in the finished test strips 10 are then built up layer-by-layer on top of base layer 18 to form the test strip structures 122. In each of FIGS. 7A and 7B, the outer shape of the test strip 10 that would be formed in the overall manufacturing process is shown as a dotted line.

The exemplary manufacturing process employs base layer 18 covered by conductive layer 20. Conductive layer 20 and base layer 18 can be in the form of a reel, ribbon, continuous web, sheet, or other similar structure. Conductive layer 20 can include any suitable conductive or semi-conductor material, such as gold, silver, palladium, carbon, tin oxide and others known in the art. Conductive layer 20 can be formed by sputtering, vapor deposition, screen printing or any suitable manufacturing method. For example, one or more electrodes may be at least partially formed by sputtering, evaporation, electroplating, ultrasonic spraying, pressure spraying, direct writing, shadow mask lithography, lift-off lithography, or laser ablation. Also, the conductive material can be any suitable thickness and can be bonded to base layer 18 by any suitable means.

As shown in FIG. 2A, conductive layer 20 can include working electrode 22, proximal electrode 24, distal electrode 28, and fill-detect cathode 30. Trace 80 can be formed by laser ablation where laser ablation can include any device suitable for removal of the conductive layer in appropriate time and with appropriate precision and accuracy. Various types of lasers can be used for sensor fabrication, such as, for example, solid-state lasers (e.g. Nd:YAG and titanium sapphire), copper vapor lasers, diode lasers, carbon dioxide lasers and excimer lasers. Such lasers may be capable of generating a variety of wavelengths in the ultraviolet, visible and infrared regions. For example, excimer laser provides wavelength of 248 nm, a fundamental Nd:YAG laser gives 1064 nm, a frequency tripled Nd:YAG wavelength is at 355 nm and a Ti:sapphire laser is at approximately 800 nm. The power output of these lasers may vary and is usually in range 10-100 watts.

The laser ablation process can include a laser system. The laser system can include a laser source. The laser system can further include means to define trace 80, such as, for example, a focused beam, projected mask or other suitable technique. The use of a focused laser beam can include a device capable of rapid and accurate controlled movement to move the focused laser beam relative to conductive layer 20. The use of a mask can involve a laser beam passing through the mask to selectively ablate specific regions of conductive layer 20. A single mask can define test strip trace 80, or multiple masks may be required to form test strip trace 80. To form trace 80, the laser system can move relative to conductive layer 20. Specifically, the laser system, conductive layer 20, or both the laser system and conductive layer 20 may move to allow formation trace 80 by laser ablation. Exemplary devices available for such ablation techniques include Microline Laser system available from LPKF Laser Electronic GmbH (Garbsen, Germany) and laser micro machining systems from Exitech, Ltd (Oxford, United Kingdom).

In the next step, dielectric-spacer layer 64 can be applied to conductive layer 20, as illustrated in FIG. 2B. Spacer 64 can be applied to conductive layer 20 in a number of different ways. In an exemplary approach, spacer 64 is provided as a sheet or web large enough and appropriately shaped to cover multiple test strip traces 80. In this approach, the underside of spacer 64 can be coated with an adhesive to facilitate attachment to conductive layer 20. Portions of the upper surface of spacer 64 can also be coated with an adhesive in order to provide adhesive layer 78 in each of the test strips 10. Various sample chambers can be cut, formed or punched out of spacer 64 to shape it before, during or after the application of spacer layer 64 to conductive layer 20. In addition, spacer 64 can include adhesive sections 66, with break 84 there between, for each test strip trace 80. Spacer 64 is then positioned over conductive layer 20, as shown in FIG. 2B, and laminated to conductive layer 20. When spacer 64 is appropriately positioned on conductive layer 20, exposed electrode portions 54-62 are accessible through sample chambers 52 and 58. Similarly, spacer 64 leaves contacts 32-38 and auto-on conductor 48 exposed after lamination.

Alternatively, spacer 64 could be applied in other ways. For example, spacer 64 can be injection molded onto base layer 18 and dielectric 50. Spacer 64 could also be built up on dielectric layer 50 by screen-printing successive layers of a dielectric material to an appropriate thickness, e.g., about 0.005 inches. A preferred dielectric material comprises a mixture of silicone and acrylic compounds, such as the "Membrane Switch Composition 5018" available from E.I. DuPont de Nemours & Co., Wilmington, Del. Other materials could be used, however.

Additionally, sample chambers can be formed after application of the spacer 64 on top of base layer 18 and conductive layer 20 via the aforementioned laser ablation process. This process allows for the removal of the conductive layer within sample chambers.

Reagent layer 25 can then be applied to each test strip structure. In an illustrative approach, reagent layer 25 is applied by dispensing a formulation onto exposed portion 54 of working electrode 22 and letting it dry to form reagent layer 25. Alternatively, other methods, such as screen-printing, spray deposition, piezo and ink jet printing, can be used to apply the composition used to form reagent layer 25.

An exemplary formulation contains 100 mM potassium phosphate at pH 7.25, 175-190 mM ruthenium hexamine, 5000 U/mL glucose dehydrogenase, 0.5-2.0% methocel, 0.025-0.20% trehalose 250M (hydroxyethylcellulose), 0.675-2.5% sucrose (microcrystalline cellulose), 0.05-0.20% Triton-X surfactant and 2.5-5.0% trehalose. In some embodiments, various constituents may be added to reagent layer 25 to at least partially reduce a hematocrit bias of any measurement. For example, various polymers, molecules, and/or compounds may be added to reagent layer 25 to reduce cell migration and hence may increase the accuracy of a measurement based on an electrochemical reaction. Also, one or more conductive components may be coated with a surface layer (not shown) to at least partially restrict cell migration onto the one or more conductive components. These and other techniques known in the art may be used to reduce hematocrit bias from any measurement.

A transparent cover 72 can then be attached to adhesive layer 78. Cover 72 may be large enough to cover multiple test strip structures 122. Attaching cover 72 can complete the formation of the plurality of test strip structures 122. The plurality of test strip structures 122 can then be separated from each other to form a plurality of test strips 10, as described above.

Quality Control Testing of Test Strips

Figure 9:
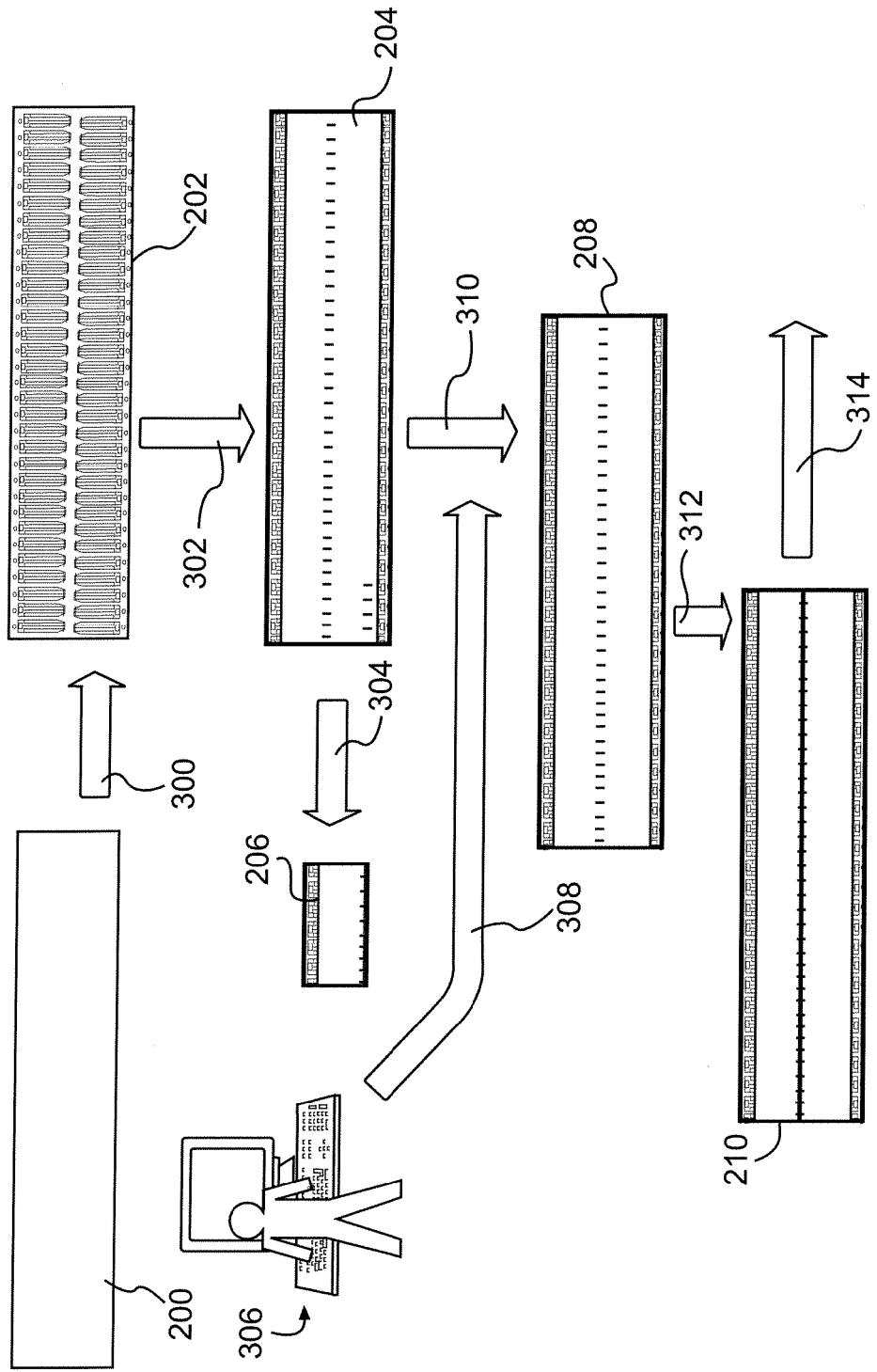
FIG. 9 is a diagram of the manufacturing process before production testing according to a further illustrative embodiment of the invention.

FIG. 9 shows a further illustrative embodiment of a test strip manufacturing method. The manufacturing method utilizes a web 200 containing conductive layer 20 and base layer 18. Conductive layer 20 and base layer 18 can be any suitable material. Web 200 can be any dimension suitable for production of the test strips. Web 200 is passed through any suitable device and ablated by process 300.

Ablation 300 can include any suitable ablation process capable of forming conductive components in conductive layer 20. In the illustrative embodiment, ablation 300 is achieved by laser ablation. The ablation process may not electrically isolate all conductive components. For example, counter electrode 24 may not be isolated by laser ablation but can be isolated by subsequent separation from web 200. In the illustrative embodiment, working electrode 22 is electrically isolated during ablation process 300. The proximal electrode 24, distal electrode 28 and fill-detect cathode 30 may not be electrically isolated during ablation process 300. Specifically, subsequent separation process can electrically isolate the proximal electrode 24, distal electrode 28 and fill-detect cathode 30.

Web 200 can be passed through any suitable ablation device at speeds sufficient to produce an appropriate rate of test strip production. The ablation process can be sufficiently rapid to allow the continuous movement of web 200 through the laser ablation device. Alternatively, web 200 can be passed through the ablation device in a non-continuous (i.e., start-and-stop) manner.

The properties of the conductive components formed by ablation process 300 can be analyzed during or following ablation process 300. Analysis of ablation process 300 can include optical, chemical, electrical or any other suitable analysis means. The analysis can monitor the entire ablation process, or part of the ablation process. For example, the analysis can include monitoring vector formation to ensure the dimensions of the formed vector are within predetermined tolerance ranges.

Quality control analysis, which can be performed during or upon completion of the manufacturing process, can also include monitoring the effectiveness and/or efficiency of the vector formation process. In particular, the width of the resulting vectors can be monitored to ensure acceptable accuracy and precision of the cuts in conductive layer 20. For example, the quality of the laser ablation process can be analyzed by monitoring the surface of conductive layer 20 and/or base layer 18 following ablation. Partial ablation of base layer 18 can indicate that the laser power is set too high or the beam is traveling too slowly. By contrast, a partially ablated conductive layer may indicate insufficient laser power or that the beam is traveling too quickly. Incomplete ablation of gaps may result in the formation of vectors that are not electrically isolating between conductive components.

In the illustrative embodiment, the dimensions of working electrode 22 can be analyzed to determine the quality of the manufacturing process. For example optical analysis (not shown) can monitor the width of working electrode 22 to ensure sufficient accuracy of ablation process 300. Further, the alignment of working electrode 22 relative to registration points 102 can be monitored. Optical analysis can be performed by using VisionPro system from Cognex Vision Systems (Natick, Mass.).

As described above, the ablation process produces an array of test strips 202 on web 200. Following formation of test strip array 202 and corresponding conductive components, dielectric-spacer layer 64 is laminated to conductive layer 20. The spacer lamination process 302 can include registration points 102 to correctly align spacer layer 64 with conductive layer 20. Spacer 64 may contain registration points 102 corresponding to registration points 102 of test strip array 202.

Test card 206 can be analyzed by test card analysis process 306 to test the quality of any previous manufacturing process. Analysis 306 of test card 206 can include optical, electrical, chemical or any other suitable means for testing test card 206. In an illustrative embodiment, the electrical properties of working electrode 22 can be tested. At least one of the plurality of working electrodes 22 of test card 206 can be analyzed for electrochemical and surface properties. For example, chronoamperometry can be used to test working electrode 22. Chronoamperometry is an electrochemical technique that uses a voltage signal for excitation and measures current generated as a result of the excitation as a function of time.

Further, analysis process 306 may include measuring the width of space 26 between proximal electrode 24 and distal electrode 28 for accuracy. Additionally, a test card 104 may comprise test strips 10 in which sample chambers 52 and 58 have been formed, as discussed above. Under such circumstances analysis process 306 may include testing at least one of sample chambers 52 and 58 to determine if they have the dimensions that fit within predetermined tolerances, for example.

The results of analysis 306 can be compared to previous manufacturing process. Alternatively, the results of analysis 306 may be compared to modeled or simulated results using computational methods. The results can be used to ensure high-quality manufacturing processes. Deviation from acceptable or expected results may require altering upstream manufacturing processes, or altering downstream manufacturing processes to address the deviations. Following acceptance of the results of analysis 306, the quality of upstream manufacturing processes can be confirmed.

Following satisfactory feedback 308 from test card analysis 306, the chemistry can be applied to three-layer laminate 204 by a chemistry application process 310. The resulting laminate 208 can contain any appropriate reagent suitable for the specific test strip. The reagent application process 310 can include any appropriate process. In the preferred embodiment, quality control testing is not performed following reagent application 310. In other embodiments, quality control testing can be conducted following chemistry application 310. For example, quality control analysis can monitor the effectiveness of the chemistry application. Specifically, optical analysis may be required to determine the extent of reagent covering working electrode 22 and/or counter electrode 24. Alternatively, any previous or upstream manufacturing process can be tested following formation of laminate 208.

Following reagent application 310, cover 72 can be applied to laminate 208 using any appropriate cover application process 312. Cover 72 may be centered on laminate 208. The resulting laminate 210 can be tested to ensure the quality of the cover application process 312. For example, optical means can be used to monitor the alignment of the cover to laminate 208. Alternatively, laminate 210 can be tested to ensure the quality of any upstream manufacturing process as described previously. Following cover application 312, laminate 210 can be moved to production testing 314.

The manufacturing process can be halted at any stage based upon the results of the quality control testing during manufacturing or production. Alternatively, one or more manufacturing processes can be adjusted based on the results of the quality control analysis. Quality control tests can be conducted in real time, and/or may include analysis of test cards removed from the production line. If the quality control testing is performed on test cards taken out of the production line, any production of the same lot or batch can be intercepted in the manufacturing process downstream of the quality control testing. Test card 206 can contain addressable information, identifying where the test card was removed from the production line. Consequently any deviations from appropriate manufacturing quality can be isolated to specific regions of the production line.

CONCLUSION

In summary, determining multiple blood analyte levels in separate sample chambers is desirable. Since measuring the level of certain blood analytes require the measurement to occur within a sample cavity which includes a chemistry solution, while other blood analytes do not, it is important to control the distribution of the chemical solution within a sample chamber. Thus, the use of methods and systems relating to sacrificial-spacer layers, surface modifications, chemical dams, and spacer dams, are useful in selectively applying a biosensor reagent to a single sample cavity, within a multiple sample cavity biosensor.

While various test strip structures and manufacturing methods are described as possible candidates for use to measure hematocrit and to selectively apply a biosensor reagent to a single sample cavity, they are not intended to be limiting of the claimed invention. Unless expressly noted, the particular test strip structures and manufacturing methods are listed merely as examples and are not intended to be limiting of the invention as claimed. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for manufacturing a biosensor for detecting one or more analytes in a fluid sample, comprising:
    a generally planar base layer having a proximal end and a distal end;
    depositing a conductive layer on the base layer, the conductive layer comprising a plurality of electrodes disposed on the base layer near the proximal end, and a plurality of electrical contacts disposed on the base layer near the distal end;
    forming a first capillary chamber on the base layer having a first opening at the proximal end, wherein the first capillary chamber includes at least a working electrode and a counter electrode selected from the plurality of electrodes, wherein the working electrode and the counter electrode are configured to operate in conjunction to detect the one or more analytes in the fluid sample;
    forming a second capillary chamber having a second opening at the proximal end separate from the first opening, wherein the second capillary chamber is configured to include at least one electrode selected from the plurality of electrodes excluding the working electrode; and
    forming a reagent layer on the base layer, the reagent layer formed to at least partially cover the first capillary chamber.

2. The method of claim 1, wherein the reagent layer includes at least one of glucose oxidase, glucose dehydrogenase, potassium ferricyanide, and ruthenium hexamine.

3. The method of claim 1 further comprising forming a temporary-spacer layer configured to receive the reagent layer.

4. The method of claim 3, wherein the temporary-spacer layer comprises a pattern.

5. The method of claim 3, wherein the temporary-spacer layer is removed after deposition of the reagent layer.

6. The method of claim 5 further comprising a dielectric-spacer layer disposed on the base layer, wherein the dielectric-spacer layer defines the first and second capillaries.

7. The method of claim 3, wherein the temporary-spacer layer comprises a thin film.

8. The method of claim 1 further comprising forming a dielectric-spacer layer disposed on the base layer, wherein the dielectric-spacer layer defines the first and second capillaries.

9. The method of claim 8, wherein the dielectric-spacer layer further comprises a spacer dam, wherein the spacer dam separates the first and second capillaries.

10. The method of claim 9 wherein the spacer dam is positioned at an entrance of the first capillary.

11. The method of claim 9 wherein the spacer dam is positioned between the first and second capillaries.

12. The method of claim 9 further comprising removing the spacer dam by one of laser ablation, chemical etching, mechanical removal, and heat embossing.

* * * * *